United States Patent
Tao et al.

(10) Patent No.: US 9,101,711 B2
(45) Date of Patent: Aug. 11, 2015

(54) INTRAVASCULAR NANO-BUBBLING OXYGENATOR

(76) Inventors: Chi-Wei Tao, Taipei (TW); Yang-Shan Yeh, Taipei (TW)

(*) Notice: Subject to any disclaimer, the term of this patent is extended or adjusted under 35 U.S.C. 154(b) by 473 days.

(21) Appl. No.: 11/868,528

(22) Filed: Oct. 7, 2007

(65) Prior Publication Data
US 2009/0093751 A1    Apr. 9, 2009

(51) Int. Cl.
*A61M 37/00*    (2006.01)
*A61M 1/16*    (2006.01)
*A61M 1/32*    (2006.01)
*A61M 25/00*    (2006.01)

(52) U.S. Cl.
CPC .............. *A61M 1/1678* (2013.01); *A61M 1/32* (2013.01); *A61M 25/007* (2013.01); *A61M 2230/06* (2013.01); *A61M 2230/20* (2013.01); *A61M 2230/205* (2013.01); *A61M 2230/50* (2013.01)

(58) Field of Classification Search
CPC .............. A61M 1/16978; A61M 1/32; A61M 2230/06; A61M 2230/20; A61M 2230/205; A61M 2230/50; A61M 25/007
USPC ............... 604/23–26, 20, 21, 103.01, 103.02, 604/264, 6.14
See application file for complete search history.

(56) References Cited

U.S. PATENT DOCUMENTS

| | | | |
|---|---|---|---|
| 5,186,713 A | 2/1993 | Raible | |
| 5,261,875 A * | 11/1993 | Spears | 604/24 |
| 5,336,164 A | 8/1994 | Snider et al. | |
| 5,376,069 A | 12/1994 | Hattler | |
| 5,407,426 A | 4/1995 | Spears | |
| 5,634,892 A | 6/1997 | Whalen | |
| 6,746,417 B2 * | 6/2004 | Spears et al. | 604/6.14 |
| 2002/0161321 A1 * | 10/2002 | Sweezer et al. | 604/6.14 |
| 2003/0138350 A1 * | 7/2003 | MacOviak et al. | 422/45 |
| 2005/0245897 A1 * | 11/2005 | Bolduc et al. | 604/524 |
| 2007/0131610 A1 * | 6/2007 | Peng et al. | 210/500.27 |
| 2011/0264031 A1 * | 10/2011 | Soltani et al. | 604/22 |

OTHER PUBLICATIONS

S.A. Conrad, J.B. Zwischenberger, J.M. Eggerstedt, Akhil Bidani, Artif Organs, Nov. 1994, 18(11):840-845, Louisiana State Univ Medical Center & Univ of Texas Medical Branch, US.
S.A. Conrad, A. Bagley, B. Bagley, R.N. Schaap, Major Findings from the Clinical Trials of the Intravascular Oxygenator, Artif Organs Nov. 1994, 18(11):846-863, USA.
W. Tao, et al., Improving Gas Exchange Performance of the Intravascular Oxygenator by Active Blood Mixing, ASIAO J., Jul.-Sep. 1994; 40(3):527-532.

(Continued)

*Primary Examiner* — Kami A Bosworth
*Assistant Examiner* — Imani Hayman
(74) *Attorney, Agent, or Firm* — Raymond Y. Chan; David and Raymond Patent Firm

(57) ABSTRACT

An intravascular nano-bubbling oxygenator includes a catheter having a tube and a separating wall dividing the tube into a first tube wall and a second tube wall and to form a first lumen and a second lumen. The first tube wall has a hydrophobic outer surface and a plurality of nano-sized first pores extending therealong. The first lumen has a closed end and a first opening end connecting to a source of gaseous oxygen. The second lumen has a second opening end and a third opening end, wherein the first lumen is capable of transporting gaseous oxygen, and the second lumen is capable of transporting liquid from the second opening end to the third opening end.

11 Claims, 3 Drawing Sheets

(56) References Cited

OTHER PUBLICATIONS

M. Tonz, L.K. Von Segesser, B. Leskosek, M.I. Turina, Quantitative Gas Transfer of an Intravascular Oxygenator, Annals of Thoracic Surgery, Jan. 1994, 57(1):146-150.
L.M. Gentilello, et al., The Intravascular Oxygenator (IVOX). Preliminary Results of a New Means of Performing Extrapulmonary Gas Exchange, J Trauma, Sep. 1993, 35(3):399-404.
C.S. Cox, Jr., Intracorporeal CO2 Removal and Permissive Hypercapnia to Reduce Airway Pressure in Acute Respiratory Failure.
J.D. Mortensen, An Intravenacaval Blood Gas Excehnage (IVCBGE) Device: A Preliminary Report, Trans Am Soc Artif Intern Organs, 1987.
J.D. Mortensen, G. Berry, Conceptual and Design Features of a Practical, Clinically Effective, Intraveneous Device (IVOX), Int. J. Artif Organs, 1989, 12(6):384-389.
J.D. Mortensen, S. Talbot, J.A. Burkart, Cross-Section Internal Diameters of Human Cervical and Femoral Blood Vessels, Jan. 1990, 226(1):115-124.
A.B. Lub, Nunn's Applied Respiratory Physiology, 5th ed., 2000.
Giorgio Cattaneo, Andreas Strauβ, Helmut Reul, Compact Intra- and Extracorporeal Oxygenator Developments, Perfusion 2004; 19: 251-255, Helmholtz Inst. for Biomed Eng, Germany.
J.B. Zwischenberger & S.K. Alpard, Artificial Lungs: a New Inspiration, Perfusion 2002; 17: 253-268, Div of Cardiothoracic Surgery, Univ of Texas Medical Branch, USA.
J.B. Zwischenberger, Weike Tao, Akhil Bidani, Intravascular Membrane Oxygenator & Carbon Dioxide Removal Devices: a Review of Performance & Improvements. ASIAO J., 1999.
T.J. Hewitt, et al., A Mathematical Model of Gas Exchange in an Intravenous Membrane Oxygenator, Ann. of Biomed. Engineer., vol. 26, pp. 166-178, 1998.
H. Kawakami, Y. Mori, J. Takagi, S. Nagaoka, T. Kanamori T. Shinbo, et al., Develop. of a Novel Polyimide Hollow Fiber for Intravascular Oxygenator, Asaio J., 1997; 43:M490.
K.M. Sim, T.W. Evans, B.F. Keogh, Clinical Strategies in Intravascular Gas Exchange, Artif Organs, Jul. 1996; 20(7):807-10. Royal Brompton Hospital, London, United Kingdom.
T. Mihaijevic, et al., Influence of Hemodynamics on the Performances of Intravascular Gas Exchangers, Ann of Thoracic Surgery, Dec. 1995, vol. 60(6):1665-1670.
Tao, W., et al.. Strategies to Reduce Surface Area Requirements for Carbon Dioxide Removal for an Intravenacaval Gas Exchange Device, ASAIO J., vol. 41 (3), pp. M567-M572, 1995.
K. Tanishita, G. Panol, P.D. Richardson, P.M. Galletti, Gas Transport in the Intracorporeal Oxygenator with Woven Tubes, Artif Organs, Nov. 1994; 18(11):797-800.
F. Brunet, J.P. Mira, C. Cerf, et al., Permissive Hypercapnia & Intravascular Oxygenator in the Treatment of Patients with ARDS, Artif Organs, Nov. 1994; 18(11):826-832.
J.R. Levick, An Introduction to Cardiovascular Physiology, 4th ed., A Hodder Arnold Publication, 2003.
D.R. Hess, et al., Respiratory Care: Priniciples & Practice, W.B. Saunders & Co., 2002.
Cattaaneo G, Compact intra- and extracorporeal oxygnator developments. Perfusion, Jul. 2004; vol. 19 (4), pp. 251-255.
Zwischenberger JB, Artificial lungs: a new inspiration. Perfusion Jul. 2002; vol. 17(4), pp. 253-268.
Zwischenberger JB, Intravascular membrane oxygenator arid carbon dioxide removal devices: a review of performance and improvements. ASAIO Journal Jan.-Feb. 1999; vol. 45(1), pp.
Todd J Hewitt, et al. A Mathemaical Model of Gas Exchange in an Intravenous Membrane Oxygenator, Ann. Biomed. Engineer. vol. 26, pp. 166-178, 1998.
Kawakami H, Development of a novel polyimide hallow fiber for an intravascular oxyenagtor. ASAIO J, Sep.-Oct. 1997; vol. 43(5) pp. M490-M494.
Sim KM, Clinical strategies in intravascular gas exchange. Jul. 1996; vol. 20(7), pp. 807-810.
Mihaljevic T, Influence of hemodynamics on the performances of intravascular gas exchanger. Ann Thorac Surg, Dec. 1995; vol. 60(6), pp. 1665-1670.
Tao W, Strategies to reduce surface area requirements for carbon dioxide removal for an intravenacaval gas exchange device. ASAIO J., Jul.-Sep. 1995; vol. 41(3), pp. M567-M572.
Tanishita K., Gas transport in the intracorporeal oxygenator with woven tubes. Artif Organs. Nov. 1994; vol. 18(11), pp. 797-800.
Brunet F, Permissive hypercapnia and intravascular oxygenators in the treatment of patients with ARDS. Artif Organs, Nov. 1994; vol. 18 (11), pp. 840-845.
Conrad SA, In vivo gas transfer performance of the intravascular oxygenator. Artif Organs, Nov. 1994; vol. 18(11), pp. 840-845.
Conrad SA, Major findings from the clinical trials of the intravascular oxygenator. Artif Organs, Nov. 18, 1994 (11), pp. 846-863.
Tao W, Improving gas exchange performance of the intravascular oxygenator by active blood mixing, ASAIO J., Jul.-Sep. 1994; vol. 40(3), pp. 527-532.
Tonz M, Quantitative gas transfer of an intravascular oxygenator. Jan. 1994; vol. 57 (1), pp. 146-150.
Gentilello LM, The intravascular oxygenator (IVOX): preliminary results of a new means of performing extrapulmonary gas exchange. J Trauma, Sep. 1993; vol. 35(3), pp. 399.
Mortensen JD (1987) An intravenacaval blood gas exchange (IVCBGE) device: a preliminary report. Trans Am Sac Artif Int Org 33: 570-573.
Mortensen JD, Berry G (1989) Conceptual and design features of a practical, clinically effective, intravenous device (IVOX). Int J Artif Organs 12: 384-389.
Mortensen JD, Talbot S, Burkart JA (1990) Cross-section internal dismeters of human cervical and femoral blood vessels: relationship to subject's sex, age, body size. Anat.
L. Andrew, Nunn's Applied Respiratory Physiology, 5th ed., 2000.
J.R. Levick, An Introduction to Cardiovascular Physiology, 4th ed., 2003.
Dean R. Hess, et al., Respiratory Care: Principles & Practice. 2002.

\* cited by examiner

INTRAVASCULAR NANO-BUBBLING OXYGENATOR

BACKGROUND OF THE PRESENT INVENTION

The annual mortality rate for all lung diseases is estimated to be approximately 250,000 in the US in 2000. About 150,000 patients were related to acute, potentially reversible respiratory failure and 100,000 patients related to chronic respiratory failure due to chronic obstructive lung disease (COPD) or chronic irreversible respiratory failure due to other illness. The estimated economic burden of these diseases is in the range of 72 billion dollars per year. The rate of death related to COPD has increased by 54%, and the World Health Organization (WHO) estimated that COPD will affect 5-15% of all adults in industrialized countries and accounting for 3 million deaths worldwide in 2020, as the $5^{th}$ most prevalent disease and the $3^{rd}$ leading cause of mortality.

The primary purpose of this design is to replace the oxygenation function of the diseased lung with acute or chronic or ventilatory impairment. Because the exchange rate of $CO_2$ by the lungs is about 200 times more than that of oxygen, the oxygenation problem is the first and most serious clinical problem for us to face. This invention is premised upon the fact that most of the clinical problems of $CO_2$ retention can be resolved simply by the patients themselves without the mechanical ventilation to increase the minute ventilation. Therefore, the Applicants simply focus the design of this invention on the resolutions for the main problem of acute, moderate to severe hypoxemia and chronic respiratory failure with long-term hypoxemia. Due to the ongoing improvement of biomaterial, the possibility of applying normal pressure to hyperbaric nano-sized pure oxygen bubbles to improve oxygenation of the intracaval deoxygenated hemoglobin is attainable. In patients with acute respiratory failure, the normal pressure to hyperbaric intravascular nano-bubbling oxygenator can replace the conventional mechanical ventilator, IVOX (intravascular oxygenator), IMO (intravenous membrane oxygenator), and/or ECMO (extracorporeal membrane oxygenator) to facilitate the oxygen demand of the patients. In patients of chronic respiratory failure, a low-flow intravenous oxygenator can replace conventional oxygen therapy system, improving the power and the motivation of patient activities.

The invention is directed at the intravascular nano-bubbling oxygenator that utilizes an intravascular catheter with numerous nano-porous surface, in order to facilitate the binding of oxygen bubbles with the deoxygenated hemoglobin of red cells in the cardiovascular system. The inventions were designed to Improve the clinical hypoxic patients with any kinds of acute or chronic lung diseases.

1. Field of Invention

The invention relates artificial to the normal pressure to hyperbaric intravascular nano-bubbling oxygenator, and more particularly to the different design of either one lumen catheter and/or multi lumens catheters with numerous nano-porous surface to facilitate the flow of nano-sized pure oxygen bubbles to the cardiovascular system.

2. Description of Related Arts

The primary purpose of the ventilation is to bring the air into and out the lungs, therefore oxygen can be added into the lungs and carbon dioxide can be removed. The volume of the pulmonary capillary circulation is about 150 ml, spreading over a surface area of approximately 750 square feet. This capillary surface area surrounds 300 million air sacs called alveoli. The deoxygenated venous return is oxygenated in less than one second in the pulmonary circulation due to huge capillary surface and extremely thin blood-alveolar barrier approximately one micrometer in distance. This allows the blood to be replenished with oxygen and for the excess carbon dioxide to be removed.

There have been numerous efforts in the past 40 years to achieve artificial ventilation function, such as negative pressure and positive pressure mechanical ventilator, and extracorporeal membrane oxygenator (ECMO).

Positive-pressure mechanical ventilation is a somewhat efficient and safe means for improving gas exchange in the patients with acute respiratory failure. However, serious adverse effects may occur with prolonged duration of intensive respiratory support or high oxygen fraction. These hazardous effects, including oxygen toxicity, barotraumas, altered hormone and enzyme systems, mechanical ventilation induced lung injury (VILI), disuse atrophy of skeleton muscles, and added to the morbidity and mortality rates for these patients.

Another approach to artificial lung function, extracorporeal membrane oxygenation (ECMO) constitutes a mechanism for prolonged pulmonary bypass, which has been developed and optimized over several decades but has limited clinical utility today as a state-of-the-art artificial lung. The ECMO system Includes an extra-corporeal pump and membrane system that performs a gas transfer across membranes. Despite the numerous advances in the implementation of ECMO over the years, its core technology is unchanged and continues to face important limitations. The limitations of ECMO include the requirement for a large and complex blood pump and oxygenator system, the necessity for a surgical procedure for cannulation, the need for systemic anticoagulation, the labor intensive implementation, the exceeding high cost, and a high rate of complications, including bleeding and infection, protein absorption, and platelet adhesion on the surface of the oxygenator membrane. As a result of these limitations, ECMO has become limited in its utility to select cases of neonatal respiratory failure, where reversibility is considered to be highly likely.

One approach to artificial lung functions has been by gas sparing or diffusion of gas across the membrane surface of hollow fibers placed within the blood supply. Previous efforts have achieved some success, and have taught much to pulmonary physiologists, but gas sparing or diffusion has not yet achieved the degree of gas exchanges optimally desired. The development of the intravascular oxygenator (IVOX) presented a natural extension in the artificial lung art since it was capable of performing intracorporeal gas exchange across an array of hollow fiber membranes situated within the inferior vena cava but did not require any form of blood pump. The insertion of the IVOX effectively introduced a large amount of gas transfer surface area (up to 600 $cm^2$) without alternation of systemic hemodynamics, unfortunately, as with ECMO, the IVOX system has numerous limitations including a moderate rate of achievable gas exchange, difficulty in device implantation, a relatively high rate of adverse events, and a significant rate of device malfunctions, including blood-to-gas leaks due to broken hollow fibers.

Clinically, there is still a long way to go for us to achieve perfect artificial oxygenation whether in acute patients or long-term care. Therefore, a serious need exists for new technology and therapeutic approaches that have the potential to provide acute, intermediate to chronic, and long-term respiratory support for patients suffering from severe pulmonary failure. There also remains a paramount need for an efficient and inexpensive technology to achieve sustained oxygen concentration in the blood, thereby bypassing the diseased lung without resorting to further damage.

SUMMARY OF THE PRESENT INVENTION

Accordingly, an object of the present invention is to provide a normal pressure to hyperbaric intravascular nano-bubbling oxygenation system comprising a catheter with single or multi-lumens, a tube wall with numerous nano-sized pores on its surface, capable of being inserted into a blood vessel to transport gas.

DETAILED DESCRIPTION OF THE FIRST EMBODIMENT

Figure 1A:
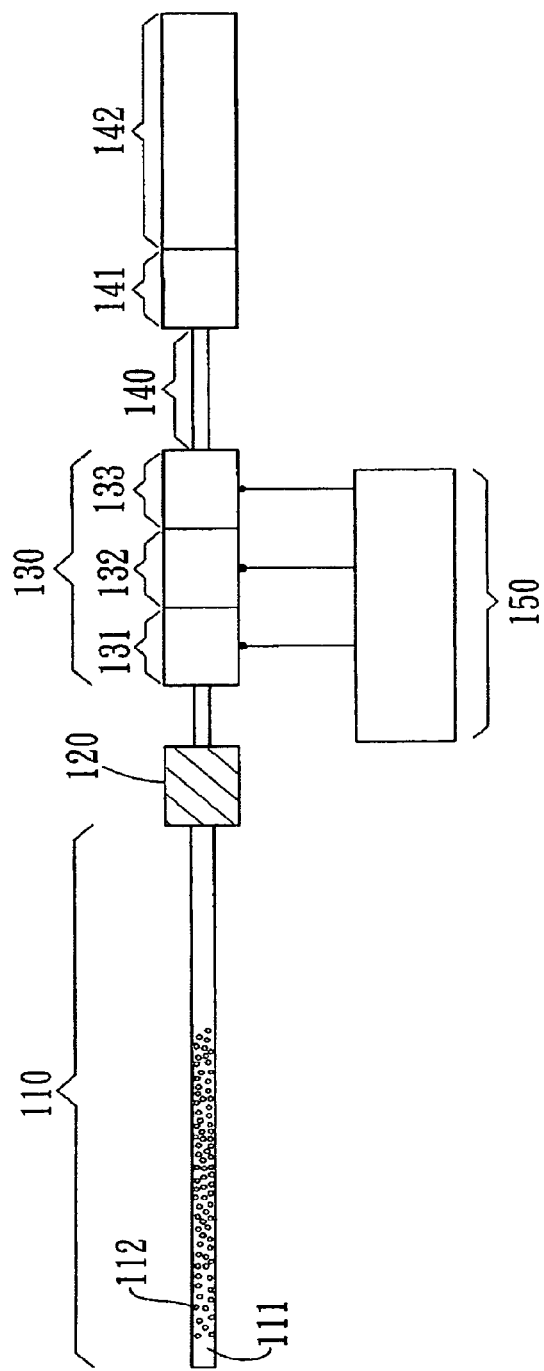
FIG. 1A, 1B, it is an embodiment of the present invention to illustrate the normal pressure to hyperbaric intravascular nano-bubbling oxygenator of one lumen type.
Figure 1B:
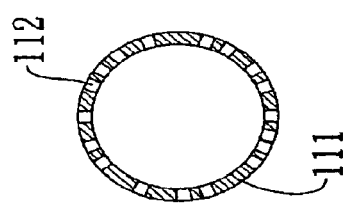

We presently contemplate that the embodiment of FIGS. 1A and 1B to be an embodiment of the present invention to illustrate a one lumen type of a normal pressure to hyperbaric intravascular nano-bubbling oxygenator. A partial porous catheter 110 comprises a tube wall 111 having a plurality of pores 112. The catheter 110 is capable of being inserted into a blood vessel. The cross-section area of the catheter 110 is less than three fourths (¾) of the cross-section area of the blood vessel. The length of the catheter 110 in a blood vessel varies from person to person depending on patient's body size. The catheter 10 comprises the biomaterial, such as, polymer, or ceramic, or metal, or composites, but other materials are also suitable. The tube wall 111 is hydrophobic and able to prevent bacterial colonization and thrombogenesis. The porous area portion of the tube wall 111 is five (5)% to nine-nine (99)% of the entire catheter in the blood vessel. The sizes of the pores range from 0.3 nanometer to five hundred (500) micrometer.

The catheter 110 includes one closed end and one opening end. The opening end is connected to a connector 120.

The connector 120 connects the catheter 110 and the gas transporting apparatus 130. The gas transporting apparatus 130 comprises a couple with or without an extended tube and a filter (not shown) for the connection with the connector 120. The gas transporting apparatus 130 comprises a flow adjustor 131 with a flow sensor (not shown), a pressure adjustor 132 with a barometer (not shown), a thermo adjustor 133 with a thermometer (not shown) for these range parameters.

The catheter 110 includes one dosed end and one opening end. The opening end is connected to a connector 120.

Figure 2A:
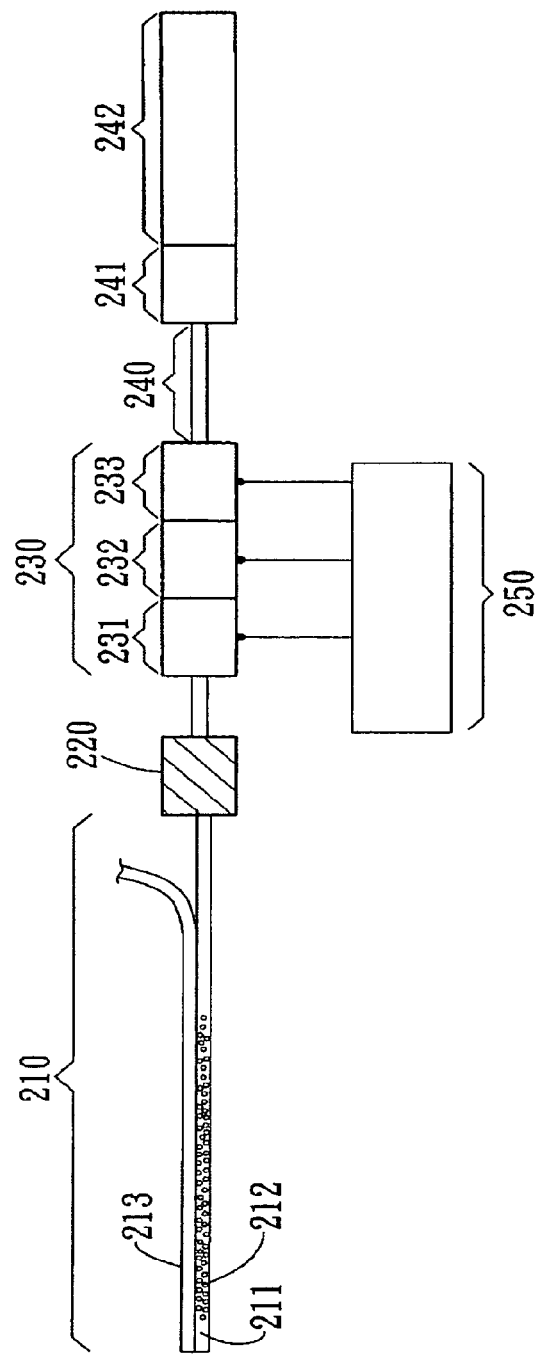
FIG. 2A, 2B, it is an embodiment of the present invention to illustrate the normal pressure to hyperbaric intravascular nano-bubbling oxygenator of multi lumens type.
Figure 2B:
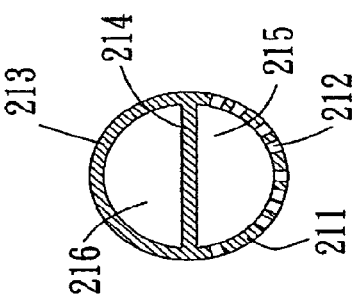

We presently contemplate that the embodiment of FIGS. 2A and 2B to be an embodiment of the present invention to illustrate a normal pressure to hyperbaric intravascular nano-bubbling oxygenator of multiple lumens type. A partial porous catheter 210 comprises two lumens, one lumen tube wall 211 having lots of pores 212; the other lumen tube wall 213 with or without pores, and a separating wall 214 to separate the tube 210 into the gas lumen 215 with pores on outer tube wall and the liquid lumen 216 with or without pores on the outer tube wall. Each of the gas lumen 215 and the liquid lumen 216 with a removable cap (not shown) has an opening end and the gas lumen 215 connects to a connector 220. The other end of the liquid lumen 216 comprises an opening end to allow the guide wire or liquid passing through it. The other end of the gas lumen 215 comprises a closed end. The catheter 210 is capable of being inserted into a blood vessel. The cross-section area of the catheter 210 is less than three fourths (¾) of the cross-section area of the blood vessel. The length of the catheter 210 in a blood vessel varies from person to person depending on patient's body size. The catheter 210 comprises the biomaterial, such as, polymer, or ceramic or metal, or composites. The tube wall 211 and tube wall 213 are hydrophobic and able to prevent bacterial colonization and thrombogenesis. The porous area portion of the tube wall 211 ranges from five (5%) to ninety-nine (99%) of the entire tube that is inserted into a blood vessel whereas the porous area portion of tube wall 213 ranges from zero (0)% to ninety-nine (99)% of the entire tube in the blood vessel. The sizes of these pores 212 range from zero point three (0.3) nanometer to five hundred (500) micrometer.

The connector 220 connects the gas lumen 215 of the catheter 210 and the gas transporting apparatus 230. The gas transporting apparatus 230 comprises a couple with or without an extended tube and a filter (not shown) for the connection with the connector 220. The gas transporting apparatus 230 comprises a flow adjustor 231 with a flow sensor (not shown), a pressure adjustor 232 with a barometer (not shown), a thermo adjustor 233 with a thermometer (not shown) for range parameters.

A pipe 140 connects the gas transporting apparatus 130 and a high pressure gas tank or any other container 142 with a regulator 141. In an embodiment, the gas is oxygen. The regulator 141 works as one of the main switches to allow the oxygen to be transported into the normal pressure to hyperbaric intravascular nano-bubbling oxygenator. The thermo adjustor 133 warms or cools the oxygen to a proper temperature, the pressure adjuster 132 adjusts the pressure of the oxygen, and the flow adjustor 131 controls the flow rate of the oxygen. The oxygen passes the connector 120 to the tube 110, and then distributes through the plurality of pores 112 into the blood. The plurality of pores 112 help produce bubbles in a range of nanometer to micrometer scale for range parameters when transporting gas.

The control panel 150 calculates the feedback of the measurement of the blood oxygen concentration, vena cava pressure, heart rate, and temperature by one or one more detectors (not shown) and controls the gas transporting apparatus 130 for transporting gas at the specific range of temperature, pressure, and flowrate to the catheter 110 through the connector 120.

Figure 3:
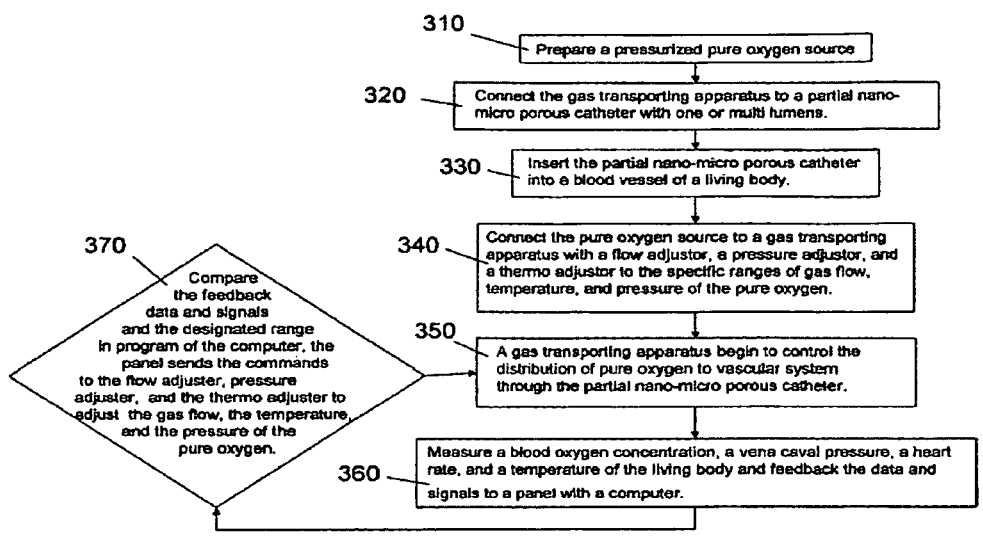
FIG. 3, it is the flowchart to illustrate the method for oxygenation.

Referring to FIG. 3, it is the flowchart to illustrate the method for oxygenation. At step 310, a pressurized pure oxygen source is prepared. The oxygen source may be tank containing pressurized pure oxygen. At step 320, a gas transporting apparatus, including a flow adjuster, a pressure adjuster, and a thermal adjuster to control the range parameters of the gas flow, temperature, and pressure of the oxygen, is connected to a gas lumen of a porous catheter with nano to micro-meter sized pores. At step 330, the oxygen source is connected to the gas transporting apparatus. At step 340, the porous catheter is inserted into a blood vessel of a living body. At step 350, the gas transporting apparatus controls the distribution of the oxygen to the vascular system through the porous catheter. At step 360, a blood oxygen concentration, a vena caval pressure, a heart rate, and a temperature of the living body are measured to as the control signals to feedback to the computer in a panel. At step 370, the control signals are compared with the predetermined ranges set in the computer, and the panel sends commands to the gas transporting apparatus, and then back to the step 350.

One skilled in the art will understand that the embodiment of the present invention as shown in the drawings and described above is exemplary only and not intended to be limiting.

The foregoing description of the preferred embodiment of the present invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. An intravascular nano-bubbling oxygenator, comprising:
a catheter comprising a tube and a separating wall extended inside said tube to divide said tube into a first tube wall and a second tube wall and to form a first lumen within said first tube wall and said separating wall, and a second lumen within said second tube wall and said separating wall, wherein said first tube wall has a hydrophobic outer surface and comprises a plurality of nano-sized first pores extending therealong, which are provided with sizes ranging from 0.3 nanometer to 500 micrometer; wherein said first lumen comprises a closed end, and a first opening end connecting to a source of gaseous oxygen, said second lumen comprises a second opening end and a third opening end, said first lumen capable of transporting gaseous oxygen, and second lumen capable of transporting liquid from said second opening end to said third opening end; wherein said catheter is capable of being inserted into a blood vessel and has a cross-section area less than three fourths of the cross-section area of said blood vessel, wherein said first lumen is arranged for guiding said gaseous oxygen to longitudinally flow from said opening end toward said closed end in order to transversely distribute said gaseous oxygen to produce oxygen bubbles through said nano-sized pores directly inside said blood vessel.

2. The intravascular nano-bubbling oxygenator of claim 1, wherein said first tube wall, second tube wall and separating wall comprise biomaterial.

3. The intravascular nano-bubbling oxygenator of claim 1, wherein a first porous area of said first tube wall is five (5)% to ninety-nine (99)% of said first tube wall of said catheter being inserted into said blood vessel.

4. The intravascular nano-bubbling oxygenator of claim 1, wherein a second porous area of said separating wall is zero (0)% to ninety-nine (99)% of second tube wall of said catheter being inserted into said blood vessel.

5. The intravascular nano-bubbling oxygenator of claim 1, further comprising a connector provided at said first opening end of said first lumen to input gaseous oxygen to said first lumen, said connector further comprising a gas input end.

6. The intravascular nano-bubbling oxygenator of claim 5, further comprising a gas transporting apparatus connected to said gas input end of said connector.

7. The intravascular nano-bubbling oxygenator of claim 6, wherein said gas transporting apparatus comprises a flow adjustor, a pressure adjustor, and a thermo adjuster for range parameters.

8. The intravascular nano-bubbling oxygenator of claim 6, further comprising a gaseous oxygen source connected to said gas transporting apparatus.

9. The intravascular nano-bubbling oxygenator of claim 8, wherein said gaseous oxygen source comprises a pipe, a regulator, and a gas container.

10. The intravascular nano-bubbling oxygenator of claim 6, further comprising a control panel connected to said gas transporting apparatus to control the inputting of said gaseous oxygen.

11. The intravascular nano-bubbling oxygenator of claim 10, wherein said control panel controls transporting of said gaseous oxygen by a feedback of measuring a blood oxygen concentration, a vena caval pressure, a heart rate, and a temperature.

* * * * *